United States Patent
Okanojo et al.

(10) Patent No.: US 9,091,671 B2
(45) Date of Patent: Jul. 28, 2015

(54) LIQUID SUCTION DEVICE

(75) Inventors: Masahiro Okanojo, Kokubunji (JP); Hideyuki Noda, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 260 days.

(21) Appl. No.: 13/580,674

(22) PCT Filed: Dec. 22, 2010

(86) PCT No.: PCT/JP2010/073076
§ 371 (c)(1),
(2), (4) Date: Aug. 23, 2012

(87) PCT Pub. No.: WO2011/104986
PCT Pub. Date: Sep. 1, 2011

(65) Prior Publication Data
US 2012/0321520 A1 Dec. 20, 2012

(30) Foreign Application Priority Data
Feb. 24, 2010 (JP) .................................. 2010-039247

(51) Int. Cl.
*B01L 3/02* (2006.01)
*G01N 35/10* (2006.01)
*G01N 21/64* (2006.01)

(52) U.S. Cl.
CPC ........ *G01N 35/1011* (2013.01); *G01N 21/6428* (2013.01)

(58) Field of Classification Search
CPC .............. G01N 35/10; G01N 35/1002; G01N 35/10009; G01N 35/1011; B01L 3/02; B01L 3/021; B01L 3/0237
USPC .......... 422/63–68.1, 501, 509, 511, 518, 521, 422/522, 564; 73/863.32, 864, 864.11, 73/864.23, 864.24, 864.31
See application file for complete search history.

(56) References Cited

U.S. PATENT DOCUMENTS

| | | | | |
|---|---|---|---|---|
| 5,055,263 A | * | 10/1991 | Meltzer | ............................ 422/65 |
| 5,213,766 A | * | 5/1993 | Flesher et al. | ................ 422/551 |
| 5,474,744 A | | 12/1995 | Lerch | |
| 7,988,934 B2 | * | 8/2011 | Balmer | ......................... 422/509 |

(Continued)

FOREIGN PATENT DOCUMENTS

| | | |
|---|---|---|
| JP | 59-176946 | 11/1984 |
| JP | 3-183958 | 8/1991 |

(Continued)

OTHER PUBLICATIONS

Office Action of Singapore Appln. No. 201206221-2 dated May 8, 2013 in English.

*Primary Examiner* — Brian R Gordon
(74) *Attorney, Agent, or Firm* — Jones Robb PLLC

(57) ABSTRACT

Arrangement enables liquid suction with a nozzle tip end in contact with a container bottom without causing damage to the nozzle and/or container bottom. Plural rails are disposed to extend upward from an arm which is movable three-dimensionally, so as to extend upward from the arm, and a pipe is fixed to a pipe fixing member movable along the rails. A pipe tip end functions as a nozzle. Plural resilient members disposed on the arm correct the inclination of the pipe fixing member. When the arm is moved downward and the tip end comes in contact with the bottom of the container 106, the pipe and the pipe fixing portion move upward along the rails, so that the pipe tip end can be brought into contact with the bottom surface of the container while avoiding damages in the pipe and container bottom, and to suck liquid in the container.

17 Claims, 12 Drawing Sheets

(56) References Cited

U.S. PATENT DOCUMENTS

| | | | |
|---|---|---|---|
| 8,182,745 B2 * | 5/2012 | Chiba et al. | 422/63 |
| 8,283,181 B2 * | 10/2012 | Pinkel et al. | 436/180 |
| 8,679,421 B2 * | 3/2014 | Sano et al. | 422/501 |
| 2001/0019845 A1 * | 9/2001 | Bienert et al. | 436/181 |
| 2001/0055545 A1 * | 12/2001 | Takii et al. | 422/100 |
| 2002/0146353 A1 * | 10/2002 | Bevirt et al. | 422/100 |
| 2005/0169808 A1 * | 8/2005 | Pinkel et al. | 422/100 |
| 2006/0034732 A1 * | 2/2006 | Bargh et al. | 422/100 |
| 2009/0068063 A1 * | 3/2009 | Chiba et al. | 422/68.1 |
| 2009/0272202 A1 * | 11/2009 | Uang et al. | 73/863.23 |

FOREIGN PATENT DOCUMENTS

| | | |
|---|---|---|
| JP | 2554202 | 8/1996 |
| JP | 9-21815 A | 1/1997 |
| JP | 11-271322 | 10/1999 |
| JP | 2000-55925 | 2/2000 |
| JP | 2000-88864 | 3/2000 |
| JP | 2001-321648 | 11/2001 |
| JP | 3481732 | 10/2003 |
| JP | 2005-172764 | 6/2005 |
| JP | 2007-139704 | 6/2007 |
| JP | 2009-134137 | 6/2009 |

* cited by examiner

Fig. 2A
Fig. 2B
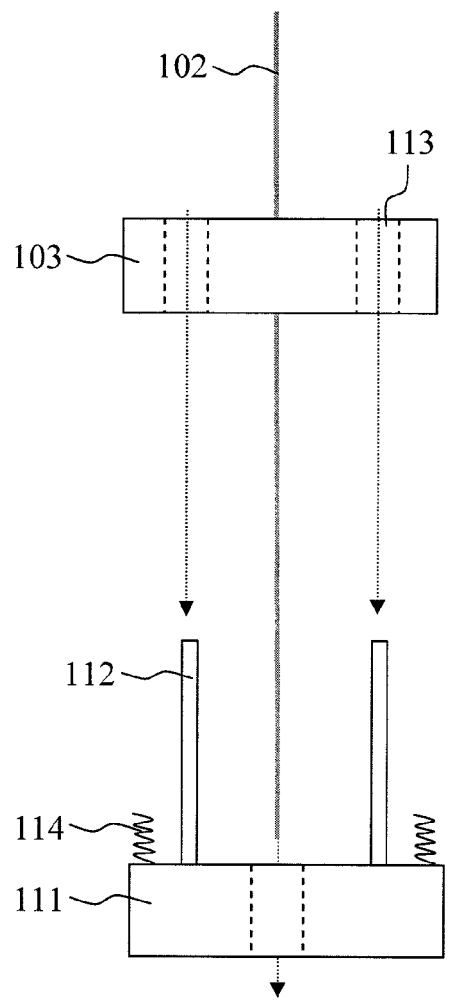
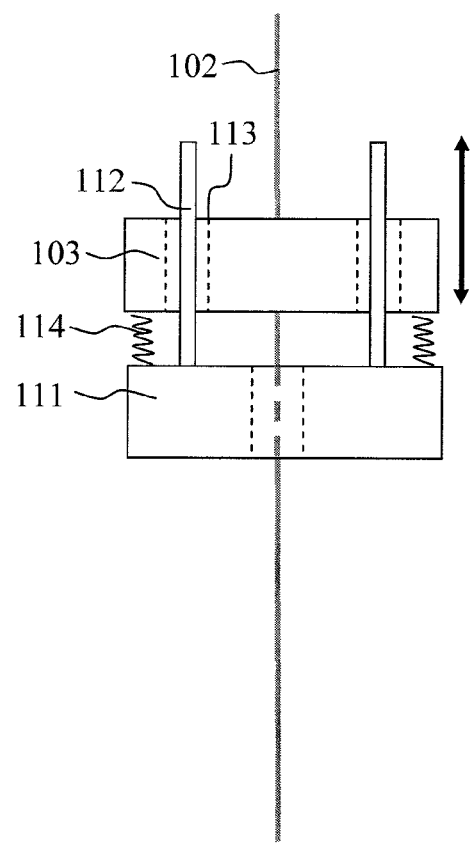

LIQUID SUCTION DEVICE

TECHNICAL FIELD

The present invention relates to a liquid suction device used for liquid suction of a sample or a reagent.

BACKGROUND ART

In an analysis or examination in the biochemical field or the immunological field, liquid of a sample or a reagent is dispensed into sample containers through a suction discharge operation. For example, in this suction discharge operation, liquid of a sample or a reagent, diluted solution, or cleaning solution stored in many small holes of many test tubes or microplates is sucked into a suction discharge nozzle, and the sucked liquid is discharged into other containers or small holes. Automation of this suction discharge operation is accomplished by implementing a suction discharge system including a suction discharge nozzle movable in the depth direction (Z direction) of a container and in the plane direction (X-Y direction) where many containers are arranged laterally and longitudinally, and a pump connecting to the nozzle via a pipe.

The suction discharge system moves the suction discharge nozzle downward into a container, and puts the nozzle tip end into liquid in the container, so as to suck the liquid. In general, at the time of moving the nozzle downward, a slight clearance is secured between the nozzle tip end and the bottom surface of the container, so as to prevent damage to the nozzle tip end and the bottom of the container due to collision therebetween. A sufficient clearance between the nozzle tip end and the bottom surface of the container facilitates positioning of the nozzle tip end in the Z direction and reduces variation in the size of sample containers due to mass production, and also reduces strictness of positioning the sample containers in the suction discharge system.

Patent Literature 1 discloses a method for preventing damage to the nozzle, and when the nozzle tip end collides with an obstacle, this method moves the nozzle and the pipe upward so that the pipe abuts to a spring-loaded earth plate, thereby stopping the aim from moving downward. Patent Literature 2 discloses a method for allowing a nozzle tip end to elastically contact with a bottom surface of a container at slow speed so as to suck slight amount of liquid stored in the container without causing deformation, damage or fatigue fracture to the nozzle and/or containers. Patent Literature 3 discloses that, for the purpose of retaining a displacement state of a relative height between a needle guide and a needle, there are provided a needle, a guide provided to the needle whose relative height is variable at a predetermined amount, means for urging the guide downward and a needle guide holder. Patent Literature 4 discloses a method of moving a movable body apart from a nozzle receiver when a nozzle tip end abuts to an obstacle, so that the nozzle moves in the reverse direction to the movement of the nozzle receiver. Patent Literature 5 discloses a method of configuring a nozzle holder for holding a nozzle to be slidable so as to adjust the reference height of the nozzle tip end relative to the X-Y plane with high accuracy.

CITATION LIST

Patent Literature

Patent Literature 1: JP 2000-55925 A
Patent Literature 2: JP 11-271322 A (1999)
Patent Literature 3: JP 2005-172764 A
Patent Literature 4: JP 2000-88864 A
Patent Literature 5: JP 2007-139704 A

SUMMARY OF INVENTION

Technical Problem

If a clearance is provided between a nozzle tip end and a bottom of a container, liquid existing in this clearance cannot be sucked, so that liquid remains in the container. For example, in the case of incorporating a liquid suction device in a measurement apparatus including an examination unit and a analyzing unit, when performing chemical reaction in the sucked liquid and measuring this liquid on the examination unit and the analyzing unit, if the liquid suction efficiency is small, the measurement sensitivity also becomes lower, where a ratio between liquid amount in a sample container before suction and liquid amount sucked in a suction discharge nozzle is defined as the liquid suction efficiency. Minimizing the clearance between a nozzle tip end and a bottom surface of a container contributes to enhancement of the liquid suction efficiency as well as enhancement of examination and analyzing sensitivities. The ideal goal is to collect the entire amount of liquid in a sample container, and there has been desired a method of bringing a nozzle tip end into contact with a bottom surface of a container in a safe manner.

It is also crucial to accurately position a nozzle tip end in the X-Y direction where many containers are arranged laterally and longitudinally. The tip end of the suction discharge nozzle is moved toward a target sample container in the X-Y direction, and then the nozzle is moved downward in the Z direction so as to suck the liquid in the sample container. If there is slight amount of liquid, accurate positioning is required particularly. Liquid becomes a hemispherical droplet if the liquid amount in the container is extremely slight, and if the suction discharge nozzle is deviated to an improper position, such a problem occurs that, when the nozzle is moved downward into the container, the nozzle is out of contact with the droplet on the bottom surface of the container and is located above a portion of the bottom surface of the container where no droplet exists, so that the nozzle cannot suck any droplet.

In recent years, it has been desired to enhance the suction operation in terms of the liquid suction efficiency and the positioning accuracy of a tip end of a suction discharge nozzle in the plane direction, in order to realize high sensitivity in an examination and analysis and to enhance processing performance per unit time (throughput) in the biochemical field and the immunological field. It is, however, difficult to enhance the liquid suction efficiency and the positioning accuracy for the following reasons.

When the nozzle tip end is positioned in the vicinity of the droplet surface, the nozzle sucks air in the vicinity of the droplet along with the droplet, which causes variation in amount of the sucked liquid. If there is a clearance between the nozzle tip end and the bottom surface of the container, the liquid existing in this clearance cannot be sucked from the nozzle tip end, so that this liquid remains in the container. In order to reduce variation in amount of the sucked liquid and reduce the residual liquid, it is necessary to bring the nozzle tip end into contact with the bottom surface of the container where a droplet exists with no clearance. Unfortunately, there is a variety of bottom surface shapes for a sample container such as a flat surface and a conical shape, and there is also a variety of materials for a bottom surface of a container, for example, in the case of detecting luminous reaction through a bottom surface of a container, the bottom surface of the container is made of a thin fused silica, or in the case of capturing microbes, a bottom surface of a container is made of a membrane filter having a thickness of several micrometers to a hundred and several tens micrometers at a hole area rate of 20 to 80%. As mentioned above, there are different shapes and materials used for a bottom surface of a container, thus the distance in the depth direction of a container and the position of a droplet on a bottom surface of a container is likely to be varied. Hence, it is difficult to reduce the clearance between a nozzle tip end and a bottom surface of a container by setting each of the length, the amount of descent, the amount of lateral and longitudinal movement of a nozzle to be a constant value. Such a constant setting causes a strong collision between the nozzle tip end and the bottom surface of the container, and may cause damage to the nozzle tip end or the bottom surface of the container. Therefore, there exists a limit of enhancing the liquid suction rate and the positioning accuracy.

For the purpose of bringing a nozzle tip end into contact with bottom surfaces of a variety of containers, specific and continuous studies were made on enhancement of the liquid suction rate and the positioning accuracy of a conventional liquid suction device. First, in order to prevent damage to a nozzle and a bottom surface of a container, a test was made in which a nozzle tip end was brought into elastic contact with a bottom surface of a container, so as to reduce impact of the contact between the nozzle tip end and the bottom surface of the container. Unfortunately, the generated elastic force functioned as a pressing force onto the bottom surface of the container, which damaged the bottom surface of the container or broke the nozzle tip end. Such damage became significant in the case of using a nozzle tip end made of capillary glass and a bottom surface made of fused silica or a membrane filter. Another test of decreasing the descendent speed was also made, which resulted in deterioration of throughput.

As a method of using no elastic object, another test was made in which a nozzle was moved downward to come in contact with a bottom surface of a container, and thereafter the entire of the nozzle was moved upward relative to the bottom surface of the container. Even this method also caused damage to the nozzle and the bottom surface of the container. Then, an LM (linear motion) guide was tried to be provided to a nozzle holder to which a nozzle is fixed so as to allow the nozzle holder movable, as described in JP 2007-139704 A. The LM guide works effectively as a means for moving the nozzle holder linearly, but when the nozzle tip end collided with the bottom surface of the container, the nozzle holder was so heavy that the nozzle tip end and the bottom surface of the container were broken before the nozzle holder slid. To counter this problem, the weight of the nozzle holder was gradually reduced so as to facilitate the nozzle holder to slide relatively smoothly. However, there still existed problems that the nozzle holder slid smoothly in some cases, but the nozzle did not slide smoothly and stopped on the way in other cases, thus the nozzle could not come in contact with the bottom surface of the container, or the nozzle tip end and the bottom surface of the container became broken, and no droplet was collected.

It was found that these problems were resulted from lateral deviation (inclination) of the nozzle at the time of moving in the X-Y-Z directions. It was also found that such inclination of the nozzle causes improper engagement in sliding, which hinders descending movement of the nozzle by its own weight or ascending movement of the nozzle when the nozzle comes in contact with the bottom surface of the container, or positional deviation of the nozzle tip end is caused by the inclination of the nozzle, which resulting in inaccurate positioning relative to the droplet, or damage or breakage to the vulnerable bottom surface of the container, or damage to the nozzle tip end or the nozzle itself if using a relatively film bottom surface of the container.

To prevent the inclination of a nozzle, it can be considered to locate a nozzle, a pipe and a pump linearly, but every time the nozzle moves, the pipe and the pump should be moved linearly along with the nozzle, which cause another problem of enlargement of the liquid suction device.

As described above, a conventional liquid suction device has problems of causing damage to a nozzle tip end and/or a bottom surface of a container or deteriorating the positioning accuracy of a nozzle tip end because of the inclination of the nozzle resulted from movement of the nozzle in the lateral, longitudinal and vertical directions.

The present invention has an object to provide a liquid suction device capable of correcting inclination of a nozzle so as to bring a nozzle tip end into contact with a bottom surface of a container without causing damage to the nozzle or the bottom surface of the container, and of enhancing positioning accuracy of the nozzle tip end, thereby enhancing the liquid suction rate.

Solution to Problem

The liquid suction device of the present invention is used in combination with some of the following solutions.

(1) The liquid suction device includes an arm movable in X-Y-Z directions, a pipe, a pipe fixing member for fixing the pipe thereto, and a pump connected to the pipe. The pipe fixing member is coupled to the arm, and the pipe fixing member can be displaced relative to the arm when the pipe opening end comes in contact with a bottom surface of a container, and an inclination correcting mechanism is provided so as to correct the inclination if the pipe fixing member is inclined relative to the arm. The nozzle is integrally formed with the pipe, and the pipe opening end is equivalent to the nozzle tip end.

(2) The relative displacement between the pipe fixing member and the arm is accomplished by providing three or more rails parallel to each other and extending upward from the arm, and inserting the rails through the through holes formed in the pipe fixing member so that the pipe fixing member can move along the rails. The inclination correction of the nozzle is accomplished by providing resilient members on or outside a polygon defined by connecting the respective positions of the rails on the arm. The resilient members are not combined with the pipe fixing member. If the pipe fixing member becomes inclined relative to the aim on the rails, the pipe fixing member pushes the resilient members, and then the resilient members pushes back the pipe fixing member, thereby correcting the inclination of the nozzle. This configuration can bring the pipe opening end (nozzle tip end) into contact with the bottom surface of the container, so as to collect the solution.

(3) The resilient members are provided in every direction in which the pipe fixing member is relatively movable, and if the pipe fixing member becomes inclined while the pipe fixing member is located on either side of the movable direction relative to the middle of the rails, the pipe fixing member pushes the resilient members disposed on the either side of the movable direction, and then the resilient members push back the pipe fixing member so as to correct the inclination.

(4) The resilient members are configured to be conductive, and the pipe fixing member is provided with a conducting layer on its surface to be in contact with the resilient members.

In this case, the plural resilient members are electrically conducted to each other through the contact between the resilient members and the pipe fixing member, and the inclination of the pipe fixing member is determined based on whether or not the resilient members are conducted to each other.

(5) The piezoelectric elements are provided at the base portions of the resilient members. In this case, if the pipe fixing member is inclined and pushes the resilient members, the piezoelectric elements detects the pressing force from the resilient members so as to detect the inclination of the pipe fixing member.

(6) It may be configured that the inclination of the pipe fixing member is detected based on whether or not the resilient members are electrically conducted to each other, or whether or not the pushing force is detected by the piezoelectric elements, and if the inclination of the pipe fixing member at a predetermined value is detected, the pipe adjustment unit corrects the inclination of the pipe fixing member.

(7) The pipe adjustment unit is disposed between the pipe fixing member and the pump. The pipe adjustment unit includes a rotor around which the pipe is wound, and adjusts the length of the pipe between the pipe adjustment unit and the pipe fixing member, so as to correct the inclination of the pipe fixing member.

(8) The liquid suction device moves the arm in the X-Y direction so as to move the pipe opening end above the sample container, and moves the arm in the Z direction so as to bring the pipe opening end in contact with the bottom surface of the sample container. At the moment of the contact, the pipe fixing member combined with the pipe moves along the rails combined with the arm, and then the liquid suction device sucks the liquid from the pipe opening end into the pipe.

(9) Before moving the arm in the X-Y-Z directions, it is confirmed whether or not the conduction is made between the resilient members, and it is determined that the pipe fixing member is located at the normal position if the conduction between the resilient members is detected; the pipe fixing member is located at the abnormal position if no conduction between the resilient members is detected. In the case of the abnormal position, the pipe adjustment unit adjusts the length of the pipe so as to correct the pipe fixing member at the normal position. If the pipe fixing member is located at the normal position, the arm is moved in the X-Y direction or in the Z direction. During the movement of the arm in the Z direction, the conduction between the resilient members is monitored, and it is determined that the pipe opening end is not contact with the bottom surface of the container while the conduction between the resilient members is being detected, so that the arm is continued to be moved in the Z direction. At the moment when no conduction between the resilient members is detected, it is determined that the pipe opening end comes in contact with the bottom surface of the container, and the movement of the arm in the height direction is stopped. Thereafter, the liquid is sucked from the pipe opening end.

(10) The resilient members are disposed not only beneath but also above the pipe fixing member. It is determined that the pipe fixing member is located at the normal position if the lower resilient members are conducted to each other, and it is determine that the pipe fixing member reaches the upper limit of the vertical movement if the upper resilient members are conducted to each other. If the conduction is made between the upper resilient members and the lower resilient members, it is determined that the pipe fixing member is inclined, and then the pipe adjustment adjusts the length of the pipe, so as to correct the inclination of the pipe fixing member.

(11) If the piezoelectric elements disposed at the base portions of the resilient members detect pressing force at the predetermined value or more, it is determined that the pipe fixing member is inclined, and then the pipe adjustment unit adjusts the length of the pipe, so as to correct the inclination of the pipe fixing member.

(12) The resilient members may be formed of springs, rubber, sponge or magnets. If the resilient members are formed of magnets, a portion of the pipe fixing member opposing the resilient members is configured to include magnets with the same pole as those of the magnets of the resilient members. The portions opposing each other between the resilient members and the pipe fixing member and between the rails may be configured to include magnets having the same pole, alternatively.

Advantageous Effects of Invention

According to the present invention, it is possible to bring the pipe opening end into contact with the bottom surface of the container without causing damage to the pipe opening end (nozzle chip end) and/or the bottom surface of the container, and collect a droplet on the bottom surface of the container efficiently. Since the pipe can be bent and the pipe fixing member is correctable even if the pipe fixing member is inclined, so that the pipe is unnecessary to be always straight, which results in size reduction of the device.

BRIEF DESCRIPTION OF DRAWINGS

FIG. 2A is an exploded view of a pipe fixing member and a rail base.

FIG. 2B is a drawing of illustrating a state in which the pipe fixing member and the rail base are assembled.

DESCRIPTION OF EMBODIMENTS

Figure 1:
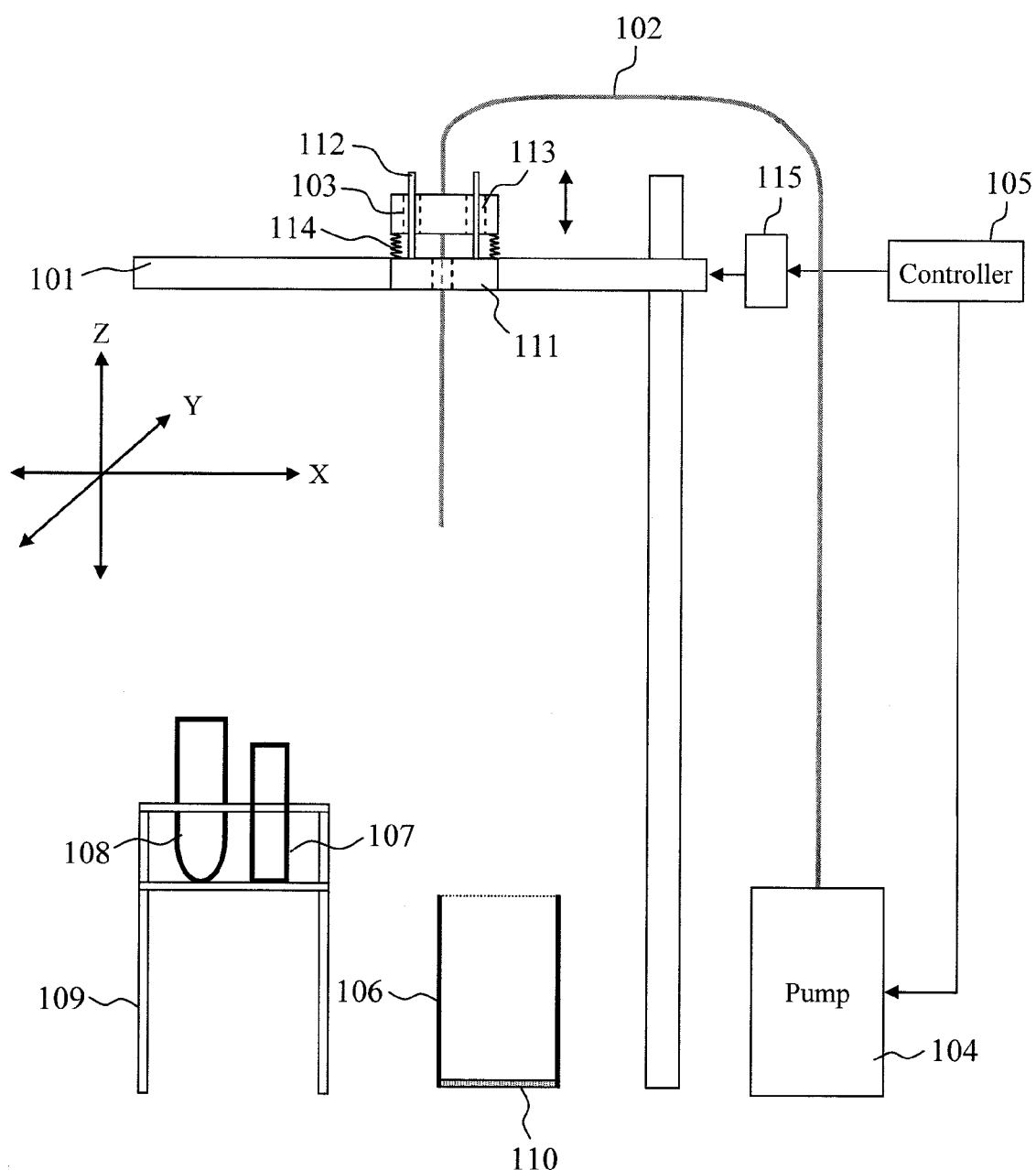
FIG. 1 is a drawing of illustrating a configuration outline of the liquid suction device.

With reference to FIG. 1, descriptions will be provided on the outline of the configuration of the liquid suction device according to the present invention. The following specific numeral values and materials and others are represented as one example of the invention, and the present invention is not limited to them.

As one example of the size and the shape of the outer frame of the liquid suction device, the liquid suction device is represented as a rectangular parallelepiped with the size of 30 cm depth×40 cm width×40 cm height. The fundamental configuration of the liquid suction device includes the arm 101 movable in the X-Y-Z directions, the pipe 102, the pipe fixing member 103 to which the pipe 102 is fixed, the pump 104 connected to a rear end of the pipe 102, the moving mechanism 115 for driving the arm 101, and the inclination correction mechanism for correcting the inclination when the pipe fixing member 103 is inclined relative to the arm 101. The moving mechanism 115 and the pump 104 are controlled by the controller 105. The liquid suction device further includes the plural sample containers 106, 107, 108 and the sample container stand 109. The sample container 106 illustrated in the drawing has the bottom surface made of the membrane filter 110. The rail base 111 is fixed to the arm 101, and the plural rails 112 are fixed to the rail base 111. The plural rails are disposed in parallel to each other.

FIG. 2A is an exploded view of the pipe fixing member 103 and the rail base 111. FIG. 2B is a drawing of illustrating a state in which the pipe fixing member 103 and the rail base 111 are assembled. As illustrated in FIG. 2A, the pipe fixing member 103 is provided with the through holes 113 vertically extending through the pipe fixing member 103, and the rails 112 are inserted in the through holes 113 as illustrated in FIG. 2B. The pipe fixing member 103 is vertically movable along the rails 112, as indicated by the vertical arrow in the FIG. 2B. Normally, the pipe fixing member 103 is in contact with the resilient members 114 disposed on the rail base 111 by its own weight, but is not combined to these resilient members 114.

Figure 3A:
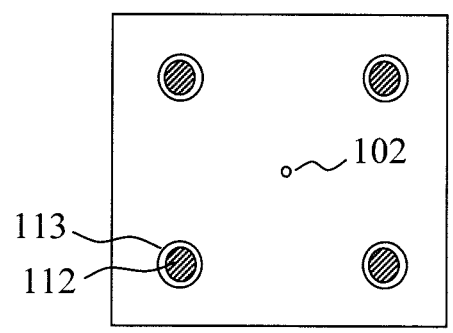
FIG. 3A is a schematic plan view of illustrating one example of the pipe fixing member.
Figure 3B:
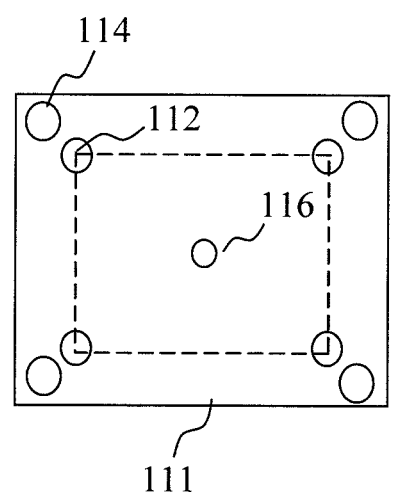
FIG. 3B is a schematic plan view of illustrating one example of the rail base.

FIG. 3A is a schematic plan view of illustrating one example of the pipe fixing member, and FIG. 3B is a schematic plan view of illustrating one example of the rail base. As illustrated in FIG. 3B, each of the resilient members 114 disposed on the rail base 111 is placed at each corner outside a rectangle defined by the four rails 112. The hole 116 is formed at the center of the rail base 111, and the pipe 102 is inserted through this hole 106. As illustrated in FIG. 3A, the four rails 112 are inserted in the respective four through holes 113 in the pipe fixing member 103, and the pipe fixing member 103 comes in contact with the resilient members 114 in such a manner that the pipe fixing member 103 covers these resilient members 114 at the four corner by its own weight. The pipe 102 is fixed at the center of the pipe fixing member 103.

The pipe 102 of the present embodiment is formed of a cylindrical glass capillary (manufactured by GL Sciences Inc.) having the length of 2 m, the inner diameter of 0.530 mm and the outer diameter of 0.660 mm. One end of the pipe 102 is connected to the pump 104, and the pipe 102 is fixed to the pipe fixing member 103 at a position of 4 cm from the other end of the pipe. The 4 cm portion from the pipe opening end to the pipe fixing member 103 functions as a nozzle and the pipe opening end functions as the nozzle end. Integration of the nozzle with the pipe simplifies the configuration of the nozzle and the pipe, and elimination of the connected face between the nozzle and the pipe stabilizes the liquid suction speed and prevents contamination from the connected face between the nozzle and the pipe.

The arm 101 can move 20 cm in the X-Y (plan) direction and 20 cm in the Z (vertical) direction.

The pipe fixing member 103 is formed in a rectangular parallelepiped of polypropylene material with the weight of 3 g and the size of 3 cm depth×1.5 cm width×0.5 cm height. Each of the four through holes 113 formed in the pipe fixing member 103 is a cylindrical hole with the diameter of 0.3 cm. The four rails 112 are disposed on the arm 101, and made of aluminum material, and each of them has the diameter of 0.28 cm. The pipe fixing member 103 is provided with the rails 112 inserted through the through holes 113, and the pipe fixing member 103 is restrained by the rails 112 so as to be movable relative to the arm 101.

The membrane filter 110 used for the bottom surface of the container was an membrane filter prepared by cutting an MF-Millipore membrane filter (manufactured by Millipore Corporation) with the pore size of 0.45 μm, the thickness of 150 μm and the porosity rate of 79%, or a Mitex membrane filter (manufactured by Millipore Corporation) with the pore size of 10 μm, and a polycarbonate filter (manufactured by Millipore Corporation) with the pore size of 0.3 μm and the thickness of 7 μm into a circular shape with the diameter of 0.5 cm, respectively. As a sample container for general use having a bottom surface other than a membrane filter, a polypropylene tube (SARSTEDT, 55.535) and a polystyrene tube (SARSTEDT, 657.462) each having a diameter of 1.2 cm were used.

Aluminum springs were used as the resilient members 114, but a sponge or rubber material may be used, instead. The resilient members 114 may be magnets, and if magnets are used as the resilient members 114, the magnets disposed on the surface of the pipe fixing member 103 opposing the resilient members 114 are configured to have the same pole as those of the magnets disposed on the resilient members 114.

With reference to FIG. 4A, FIG. 4B, FIG. 5A and FIG. 5B, descriptions will now be provided on the effect generated by the movement of the pipe fixing member 103 along the rails 112 and the inclination correcting effect.

Figure 4A:
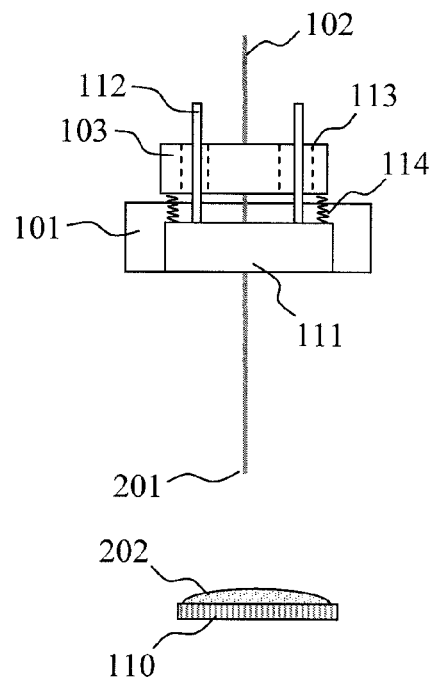
FIG. 4A is a drawing of illustrating a state in which a tip end of a nozzle is located above a droplet.
Figure 4B:
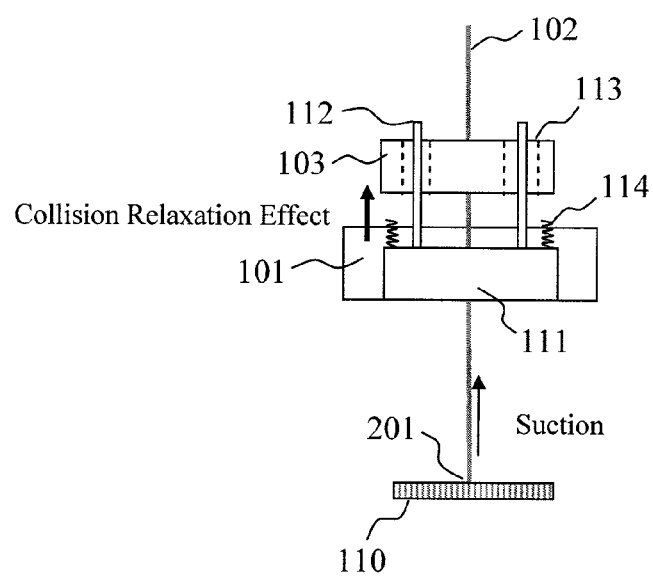
FIG. 4B is a drawing of illustrating a state in which the tip end of the nozzle collides with a membrane filter.

FIG. 4A and FIG. 4B are drawings of illustrating the effect generated by the movement of the pipe fixing member along the rails. In the state of FIG. 4A, the arm 101 is located at any height, and the pipe opening end (nozzle tip end) 201 is in contact with nowhere, and is positioned above the droplet 202 on the membrane filter 110. When the arm 101 is moved downward from the any height and while the nozzle tip end 201 is in contact with nowhere, the pipe fixing member 103 lies on the resilient members 114 and moves downward along with the arm 101. The aim 101 is continuously moved downward and when the nozzle tip end 201 collides with the membrane filter 110, the pipe fixing member 103 moves upward along the rails 112 by the distance where the arm 101 is moved downward after the collision. This movement prevents the nozzle tip end 201 and the membrane filter 110 from being damaged even if the nozzle tip end 201 collides with the membrane filter 110, thereby securely bringing the nozzle tip end 201 into contact with the membrane filter 110 (collision relaxation effect). Following this movement, the droplet 202 on the membrane filter 110 is sucked. Since the nozzle tip end 201 and the membrane filter 110 are in contact with each other, there is no clearance between the nozzle tip end 201 and the membrane filter 110, thereby attaining the efficient suction of the droplet 202.

The nozzle tip end 201 preferably has a shape other than a flat shape relative to the membrane filter 110. If the nozzle tip end 201 has a flat shape parallel to the surface of the membrane filter, the nozzle tip end 201 is buried in the membrane filter 110 after the contact of the nozzle tip end 201 with the membrane filter 110, so that it is difficult to suck the droplet 202. The nozzle tip end having an obliquely cut shape can be prevented from being buried in the membrane filter, so as to suck the droplet.

The collision relaxation effect is generated by the movement of the pipe fixing member 103 along the rails 112. Specifically, it was found that the pipe fixing member 103 is necessary to be movable vertically along the rails 112, but if the pipe fixing member 103 is inclined relative to the arm 101, friction occurs between the through holes 113 of the pipe fixing member 103 and the rails 112, which hinders the vertical movement of the pipe fixing member 103.

As a method of preventing the inclination of the pipe fixing member 103, it can be considered to configure the through holes 113 and the rails 112 to have diameters in the approximately same size, but in such a configuration, even slight inclination of the pipe fixing member 103 causes friction between the inner surfaces of the through holes 113 and the outer surfaces of the rails 112, which hinders the vertical movement of the pipe fixing member 103. The inclination of the pipe fixing member 103 affects the positioning accuracy of the nozzle tip end 201, and when the nozzle tip end 201 is brought into contact with slight amount of the droplet 202, the nozzle tip end 201 becomes inclined due to the inclination of the pipe fixing member 103 so that the nozzle tip end 201 is deviated from the position, which hinders the contact with the slight amount of the droplet; as a result no droplet is collected through the suction.

In the case of using the nozzle tip end 201 and the bottom surface of the container made of a vulnerable material such as glass capillary and a membrane filter, it is required to reduce friction and the weight of the pipe fixing member 103 as small as possible, so as to prevent the nozzle tip end 201 and the bottom surface of the container from being broken due to the friction and the weight. Note that too small friction and weight may induce the inclination of the pipe fixing member 103. The inclination of the pipe fixing member 103 is always an inevitable problem in bringing the nozzle tip end 201 into contact with the bottom surface of the container. The inclination of the pipe fixing member 103 is caused when the arm 101 moves in the X-Y direction or in the Z direction and/or when the nozzle tip end 201 comes in contact with the bottom surface of the container. In this process, the inclination of the pipe fixing member 103 should be corrected.

Figure 5A:
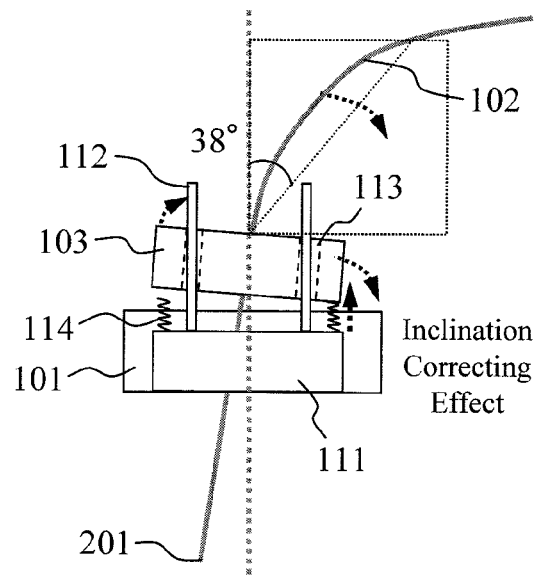
FIG. 5A is a drawing of explaining the inclination correcting effect of the pipe fixing member by using resilient members.
Figure 5B:
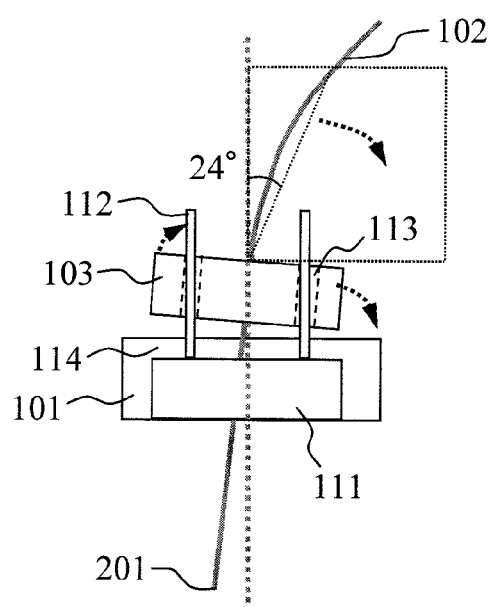
FIG. 5B is a comparative drawing of using no resilient members.

With reference to FIG. 5A and FIG. 5B, descriptions will now be provided on the inclination correcting effect of the present invention. FIG. 5A illustrates the rail base 111 with the resilient members thereon, and FIG. 5B illustrates the rail base 111 without the resilient members thereon. Defining the state of the FIG. 4A as the initial state, we focused on the inclination starting with this initial state. In the state of FIG. 4A, the nozzle tip end 201 is in contact with nowhere, and the arm 101 is located at any X-Y-Z position, and as illustrated in FIG. 3B, the resilient members 114 are disposed outside the rectangle surrounded by the rails and beneath the pipe fixing member 103. The pipe fixing member 103 is in contact with the resilient members 114 by its own weight, and the pipe fixing member 103 is not inclined in this state.

The inclination correcting effect was evaluated by using the following two methods.

(1) If the pipe 102 is held at its portion 30 cm above the pipe fixing member 103, for example, and is laterally pulled to the right, the pipe 102 is bent at its fixing point serving as a fulcrum to the right. The pipe 102 is further pulled laterally to the right, the pipe 102 is further bent to the right. Along with this movement, the pipe fixing member 103 starts to be inclined in the right direction. In the case of FIG. 5A provided with the resilient members 114, when the pipe fixing member 103 becomes inclined to the right, the resilient members 114 disposed on the right of the pipe fixing member 103 push back the pipe fixing member 103. The push back from the resilient members 114 corrects the inclination of the pipe fixing member 103.

In order to evaluate the correctable inclination angle, a rectangle was drawn to have the size of 10 cm length×5 cm width and an origin defined by the pipe position on the pipe fixing member, and the angle was calculated, which was defined by a straight line passing through the intersection point between the rectangle and the pulled pipe and the origin, and the original position (straight line) of the pipe before being pulled. In the case of providing the resilient members 114 as illustrated in FIG. 5A, even if the pipe 102 was inclined at 38°, the pipe fixing member 103 was corrected into the vertically movable state. To the contrary, in the case of providing no resilient members 114, when the pipe 102 was inclined at 24°, the pipe fixing member 103 became vertically immovable. The inclination correcting effect by providing the resilient members 114 achieved 58% improvement of the inclination.

(2) The inclination correcting effect was evaluated based on the amount of the lateral movement of the arm 101. The pipe was fixed at its portion in the vicinity of the pump 104, and the arm 101 was moved away from this fixing position in the lateral direction, so as to incline the pipe fixing member 103 and evaluate the distance in which the pipe fixing member 103 was movable vertically. In the case of providing the resilient members 114, the amount of the lateral movement was improved 70%, compared to the case of providing no resilient members 114.

The above two results show that the pipe fixing member 103 is vertically movable even if the pipe 102 is bent. Since the degree of freedom for bending the pipe increases, the pipe designing becomes more flexible by the increase of the degree of freedom, thereby realizing the size reduction of the device. The increase in amount of the lateral movement indicates the increase in movement amount of the nozzle tip end in the X-Y direction and in the Z direction, thereby significantly reducing probability of causing damage to the various parts at the time of the collision of the nozzle tip end with the bottom surface of the container due to the inclination of the pipe fixing member.

Next, a study was made on the number and the position of the rails 112 on the rail base 111. It is preferable to provide three or more rails 112. The number of the rails 112 may be two or less, and in this case, it was found that the pipe fixing member 103 was likely to be inclined and it was difficult to correct the inclination. It is preferable to dispose the respective rails 112 with the equal distance from the center of the rail base 111 and with the equal distance between the rails as well, but these distances are unnecessary to be equal so strictly.

A study was made on the installation position of the resilient members 114. It is preferable to set the installation position of the resilient members 114 on or outside the polygon defined by connecting the respective positions of the rails 112 on the rail base 111 (FIG. 3B). For example, if there are four rails 112, the resilient members 114 are preferably disposed on or outside the rectangle having apexes of the four rails 112. The resilient members 114 may also be disposed at the positions of the respective rails 112 so as to surround these rails. It is preferable that the resilient members 114 are combined to either the pipe fixing member 103 or the rail base 111, or are combined to neither of them. It was found that, if the resilient members 114 were combined to both the pipe fixing member 103 and the rail base 111, damage was caused to the nozzle tip end and/or the bottom surface of the container.

The inclination correcting effect is generated by the contact of the pipe fixing member 103 with the resilient members 114 when the pipe fixing member 103 becomes inclined. As illustrated in FIG. 4B, while the pipe fixing member 103 is apart from the resilient members 114 due to the collision relaxation effect, no inclination effect is generated because the resilient members 114 is out of the contact with the pipe fixing member 103 even if the pipe fixing member 103 becomes inclined.

To address this problem, the resilient members 301 were additionally provided above the pipe fixing member in the upward movement direction. This configuration will be described with reference to FIG. 6A to FIG. 6D. As illustrated in the FIG. 6A to FIG. 6D, the upper rail base 121 is fixed onto the upper ends of the rails 112, and the resilient members 301 are provided on the bottom face of this upper rail base. The upper resilient members 301 are disposed at the respective plural positions opposite to the respective lower resilient members 114 provided on the rail base 111. The clearance between the rail base 111 and the rail base 121 is set such that the resilient members come in contact with the pipe fixing member 103 at the time of the inclination of the pipe fixing member 103. In the present embodiment, this clearance was set to be 3 cm.

Figure 6A:
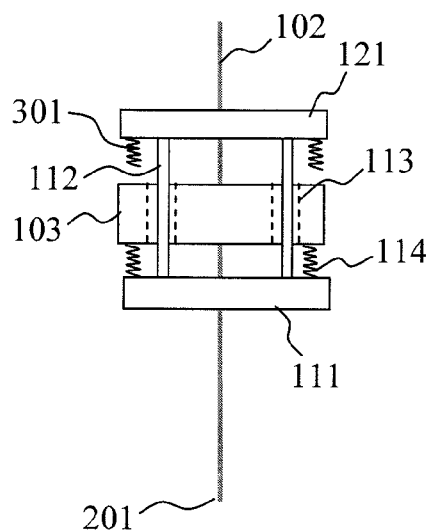
FIG. 6A is a drawing of illustrating a state in which the resilient members are disposed above and beneath the pipe fixing member, and the pipe fixing member is in contact with the lower resilient members by its own weight.
Figure 6B:
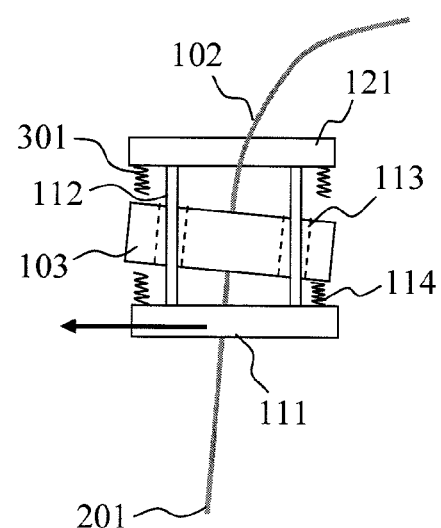
FIG. 6B is a drawing of explaining the inclination correcting effect by the lower resilient members of the pipe fixing member.

In the state of FIG. 6A, the nozzle tip end 201 is in contact with nowhere, the arm 101 is located at any X-Y-Z position, and the pipe fixing member 103 is in contact with the lower resilient members 114 by its own weight. On the other hand, the pipe fixing member 103 is out of contact with the upper resilient members 301 above the pipe fixing member 103 in the upward movement direction. If the arm 101 is laterally moved to the left from this state, the upper portion of the pipe 102 from the pipe fixing member 103 is bent to the right. If the arm 101 is further laterally moved to the left, the pipe 102 is bent to the right, and the pipe fixing member 103 is inclined to the right along with this movement. As illustrated in FIG. 6B, when the pipe fixing member 103 becomes inclined to the right, the lower resilient members 114 push back the pipe fixing member 103. This push back of the resilient members 114 corrects the inclination of the pipe fixing member 103, so that the pipe fixing member 103 is corrected into the vertically movable state along the rails 112.

Figure 6C:
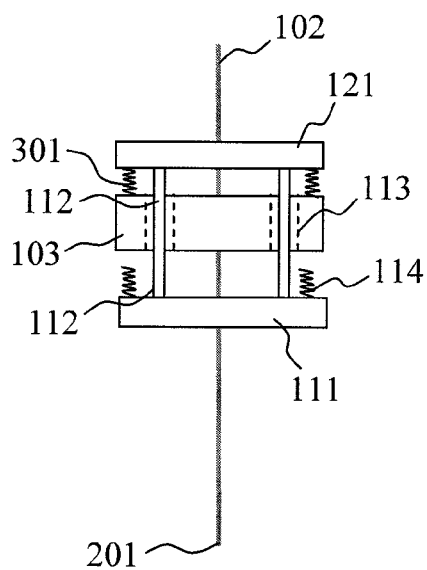
FIG. 6C is a drawing of illustrating a state in which the resilient members are disposed above and beneath the pipe fixing member, and the pipe fixing member is moved upward.
Figure 6D:
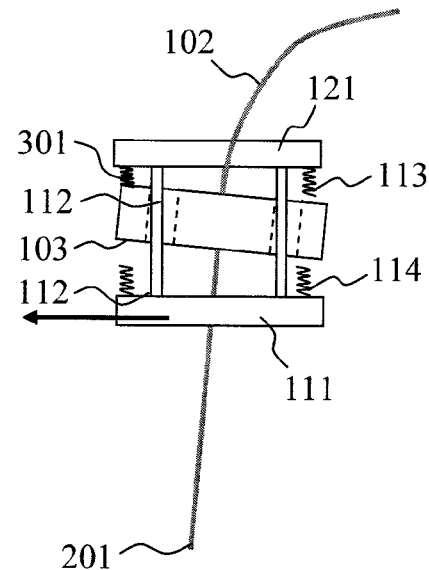
FIG. 6D is a drawing of explaining the inclination correcting effect by the upper resilient members of the pipe fixing member.

FIG. 6C illustrates the state in which the pipe fixing member 103 is moved upward, and this state indicates when the nozzle tip end 201 comes in contact with the bottom surface of the container or the very moment the nozzle tip end 201 comes apart from the bottom surface of the container. The pipe fixing member 103 is in contact with the upper resilient members 301 but is out of contact with the lower resilient members 114. If the arm 101 is laterally moved to the left in this state, the pipe 102 becomes bent to the right. If the arm 101 is further laterally moved to the left, the pipe 102 becomes bent to the right, and the pipe fixing member 103 becomes inclined rightward along with this movement. In the case of providing no upper resilient members 301, if the pipe 102 fixed to the pipe fixing member 103 becomes inclined at the angle of 20° from the position of FIG. 6C, the vertical movement of the pipe fixing member 103 along the rails 112 becomes impossible. To the contrary, in the case of providing the upper resilient members 301 above the pipe fixing member 103, if the pipe fixing member 103 becomes inclined rightward, the left resilient members 301 push back the pipe fixing member 103, as illustrated in FIG. 6D. This push back of the resilient members 301 corrects the inclination of the pipe fixing member 103, so that the pipe fixing member 103 is corrected into the vertically movable state along the rails 112 even if the pipe 102 becomes inclined at the angle of 25°. This inclination correcting effect improved the inclination by 25%.

Descriptions will now be provided on the embodiment of monitoring the position and the inclination state of the pipe fixing member 103. In some cases, the arm is needed to be moved in an environment in which the position and the inclination state of the pipe fixing member 103 cannot be confirmed visually. For example, a faint light detecting apparatus is designed to have an outer body as a dark box for preventing light from entering from outside, so as to realize high sensitivity of the detecting apparatus while preventing external light from being stored in a detecting part such as a photo multiplier in the dark box. In the case of incorporating the present invention into such an apparatus, the door of the dark box cannot be opened every time the state of the pipe fixing member 103 is confirmed. In this apparatus, it is impossible to visually check the position and the inclination state of the pipe fixing member 103 before a sample is placed in the dark box, the sample is sucked and discharged by using the liquid suction device, and the faint light detection is completed. In the worst case, if the inclination correcting effect cannot function because of a human error or the like, the only sample may be lost. To cope with this problem, it was designed to monitor the position and the inclination state of the pipe fixing member 103, surely bring the nozzle tip end 201 into contact with the bottom surface of the container, correct the inclined pipe fixing member 103 into the normal position when becoming inclined, and securely avoid a risk of causing damage to the nozzle tip end 201 and/or the bottom surface of the container.

Figure 7A:
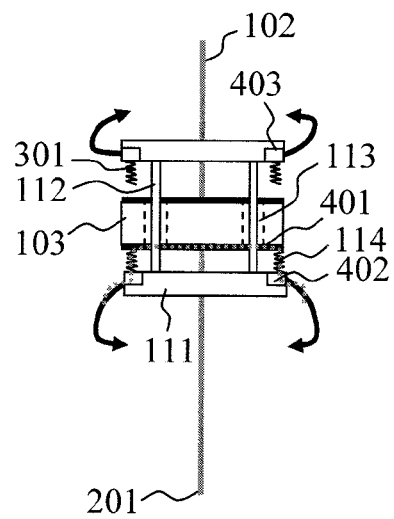
FIG. 7A is a drawing of a configuration example of detecting a position and a inclination state of the pipe fixing member.

With reference to FIG. 7A, descriptions will now be provided on the configuration example of detecting the position and the inclination state of the pipe fixing member 103. The liquid suction device includes the plural conductive resilient members 114, 301 above and below the pipe fixing member 103, and the respective resilient members are electrically connected to the controller 105. The pipe fixing member 103 is provided with the conducting layers 401 on the contact faces relative to the resilient members 114, 301, and when the resilient members 114, 301 come in contact with the pipe fixing member 103, the resilient members in contact with the pipe fixing member are electrically conducted to each other. The upper conducting layer and the lower conducting layer of the pipe fixing member 103 are also electrically connected to each other. If the pipe fixing member 103 becomes inclined, part of the lower resilient members 114 comes in contact with the lower conducting layer of the pipe fixing member 103, and part of the upper resilient members 114 also comes in contact with the upper conducting layer of the pipe fixing member 103, these upper and lower resilient members become conducted to each other through the conducting layers thereby detecting the inclination of the pipe fixing member 103. In addition, the piezoelectric elements 402, 403 are provided at the base portions of the respective resilient members 114, 301, and when the pipe fixing member 103 becomes inclined to push the resilient members, the piezoelectric elements 402, 403 detect this pressing force from these resilient members.

FIG. 7A is a drawing of illustrating that the pipe fixing member 103 is located at the reference position. The nozzle tip end 201 is in contact with nowhere, the arm 101 is located at any X-Y-Z position, and the pipe fixing member 103 is in contact with the lower resilient members 114 by its own weight. The lower conducting layer 401 on the bottom face of the pipe fixing member 103 is in contact with the resilient members 114, so that the resilient members 114 are electrically connected. Since the pipe fixing member 103 is not inclined, no pressure greatly exceeding the own weight (pressure at the predetermined value) of the pipe fixing member 103 is applied to the piezoelectric elements 402 disposed at the base portions of the resilient members 114. If the above electrical connection is detected and the pressure detected by the piezoelectric elements 402 is the predetermined value, the liquid suction device determines that the pipe fixing member 103 is at the reference position.

Figure 7B:
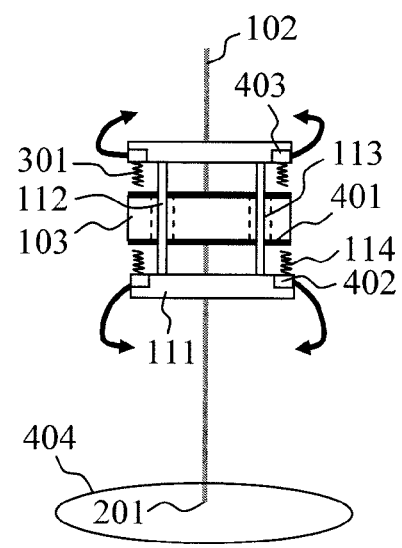
FIG. 7B is a drawing of a configuration example of detecting a position and a inclination state of the pipe fixing member.

FIG. 7B is a drawing of illustrating that the nozzle tip end 201 comes in contact with the bottom surface of the container 404, and the pipe fixing member 103 is moved upward. The pipe fixing member 103 is in contact with none of the resilient members, thus the resilient members are not electrically conducted to each other. No pressing force is applied to the piezoelectric elements disposed at the base portions of the resilient members. If there is no conduction and no pressure is detected by the piezoelectric elements, the liquid suction device determines that the pipe fixing member 103 is not inclined and the nozzle tip end 201 comes in contact with the bottom surface of the container.

Figure 7C:
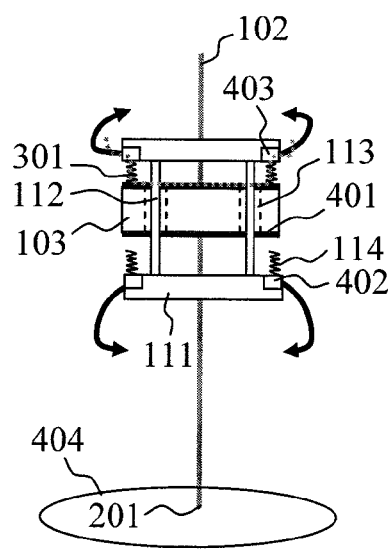
FIG. 7C is a drawing of a configuration example of detecting a position and a inclination state of the pipe fixing member.

FIG. 7C is a drawing of illustrating that the arm 101 is further moved downward after the nozzle tip end 201 comes in contact with the bottom surface of the container 404, and the pipe fixing member 103 reaches the upper limit of the upward movement. In this state, the pipe fixing member 103 is in contact with the upper resilient members 301 so that the upper resilient members 301 are electrically conducted to each other. Since the pipe fixing member 103 is not inclined, no pressing force is applied to the piezoelectric elements 403 disposed at the base portions of the resilient members 301. If such an electrical conduction is made between the upper resilient members 301 and no pressure is detected by the piezoelectric elements, the liquid suction device determines that the pipe fixing member 103 is not inclined, the nozzle tip end 201 is in contact with the bottom surface of the container, and the pipe fixing member 103 reaches the upper limit of the upward movement.

Figure 7D:
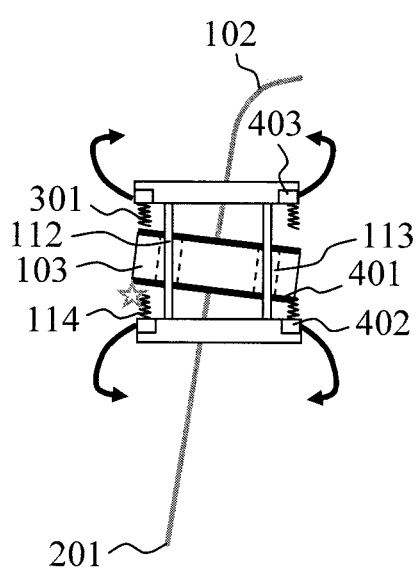
FIG. 7D is a drawing of a configuration example of detecting a position and a inclination state of the pipe fixing member.

FIG. 7D is a drawing of illustrating that the pipe fixing member 103 becomes inclined to push part of the lower resilient members 114, and the resilient members 114 push back the pipe fixing member 103, but the inclining force is greater than the pushing back force, so that the inclination correcting effect is disable. The pipe fixing member 103 is in contact with only the resilient members 114 on the inclination side. At this time, no electrical conduction is made between the resilient members 114. Since the pipe fixing member 103 is inclined, pressure much greater than the own weight of the pipe fixing member 103 is applied to the piezoelectric elements 402 disposed at the base portions of part of the lower resilient members 114. If no electrical conduction is made between the resilient members and part of the piezoelectric elements 402 detects pressure at the predetermined value or more, the liquid suction device determines that the resilient members 114 cannot function, and the pipe fixing member 103 is inclined.

Figure 7E:
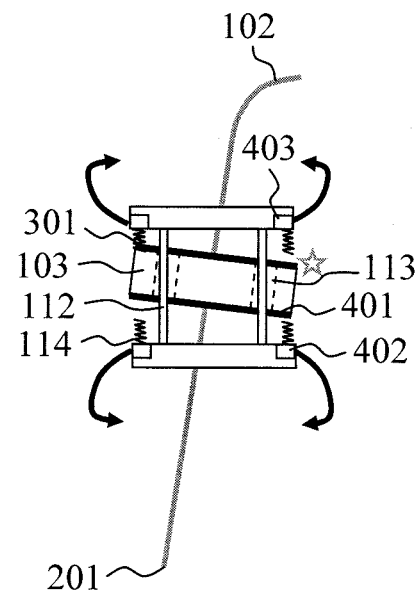
FIG. 7E is a drawing of a configuration example of detecting a position and a inclination state of the pipe fixing member.

FIG. 7E is a drawing of illustrating that the pipe fixing member 103 becomes inclined to push part of the upper resilient members 301, and the upper resilient members 301 push back the upper resilient members 301, but the inclining force exceeds the pushing back force, so that the inclination correcting effect is disable. The pipe fixing member 103 is in contact with only the upper resilient members 301 on the opposite side to the inclination side. At this time, no electrical conduction is made between the resilient members 301. Meanwhile, pressure at the specified value or more is applied to the part of the upper piezoelectric elements 403. If no electrical conduction is made and the part of the upper piezoelectric elements detects great pressure, the liquid suction device determines that the resilient members 301 cannot function and the pipe fixing member 103 is inclined.

In the embodiment of FIG. 7A to FIG. 7E, aluminum springs were used for the resilient members, and aluminum thin films were used for the conducting layers 401. Metal material or conductive polymer films may also be used for the resilient members and the conducting layers 401 as far as they are electrically conductive.

Figure 8:
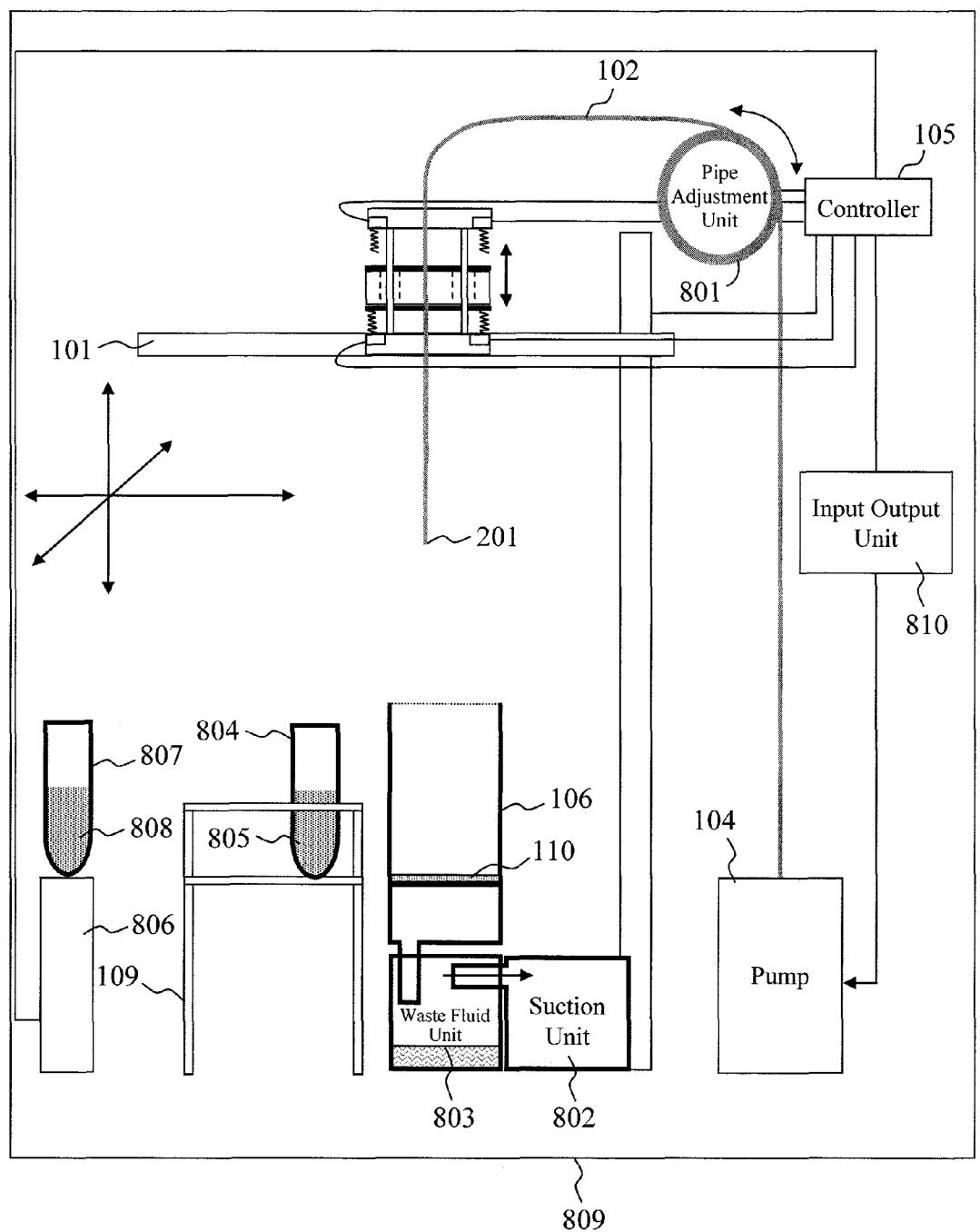
FIG. 8 is a drawing of explaining of a liquid suction device capable of microbial measurement.

In the experiments, the resilient members did not function and the pipe fixing member 103 stayed in the inclination state in some cases, as illustrated in FIG. 7D and FIG. 7E. It was found that the inclination exceeding the pushing back force of the resilient members resulted from that the pipe length between the pipe fixing member 103 and the pump was too long or too short, and an appropriate length thereof could not be maintain. To cope with this problem, there was provided the pipe adjustment unit 801 for adjusting the pipe length, as illustrated in FIG. 8. This pipe adjustment unit 801 was disposed between the pipe fixing member 103 and the pump 104. The pipe adjustment unit 801 includes a rotor, and winds the pipe 102 around the rotor, and adjusts the pipe length between the pipe adjustment unit 801 and the pipe fixing member 103 by rotating this rotor, thereby correcting the inclination of the pipe fixing member 103. Even if the pipe becomes inclined at the angle of 38° or more as illustrated in FIG. 5A, this pipe adjustment can correct the inclination by adjusting the pipe length.

Figure 9:
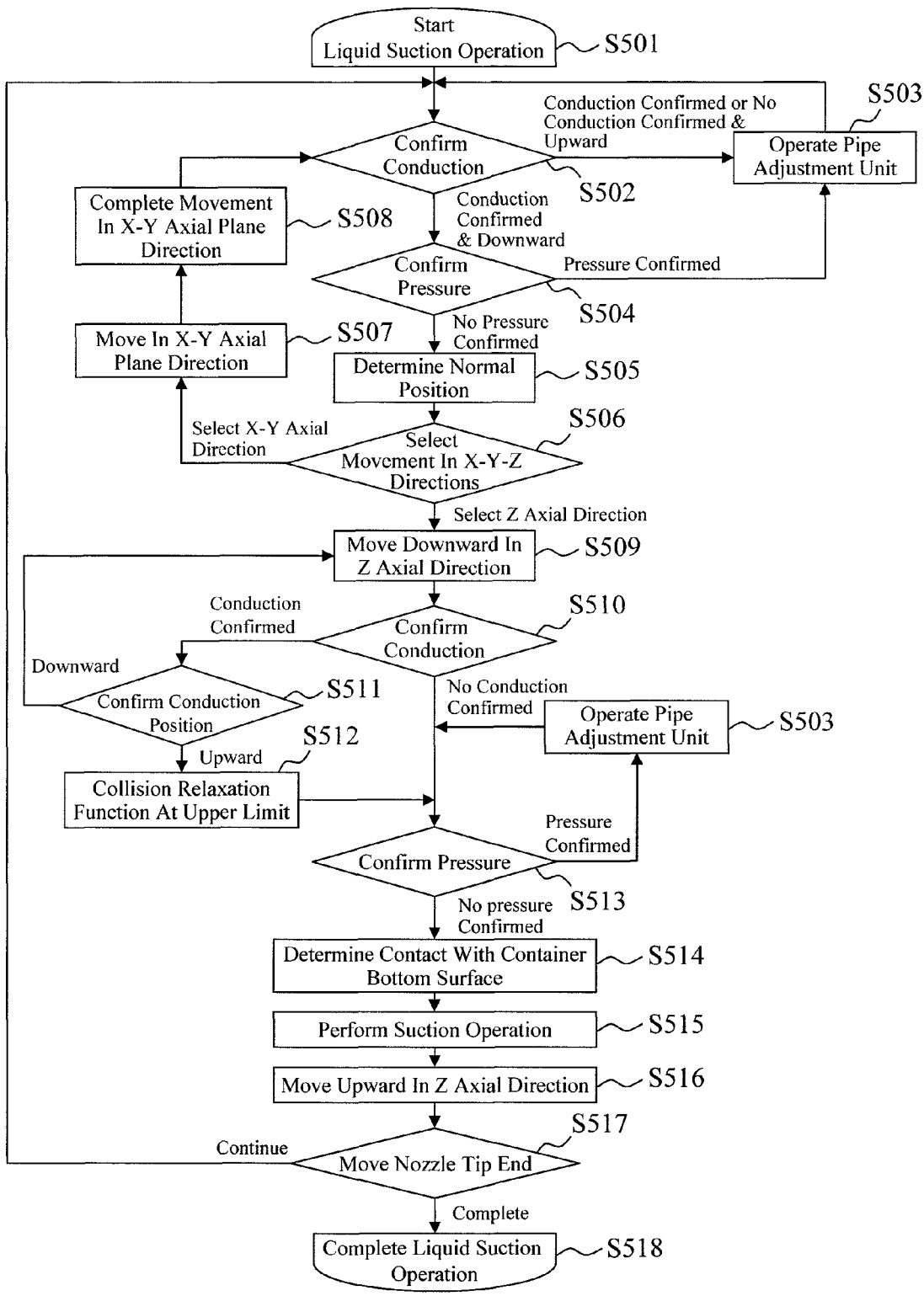
FIG. 9 is a flow chart of illustrating steps of liquid suction.

Descriptions will now be provided on how to correct the inclination of the pipe fixing member and perform the liquid suction operation appropriately, with reference to the flow chart of FIG. 9. The apparatus configuration will be described with reference to FIG. 7 and FIG. 8.

The liquid suction operation is started (S501). The liquid suction device confirms the conduction between the lower resilient members 114 (S502). If no conduction is confirmed therebetween or electric conduction is confirmed between the upper resilient members 301, it is determined that the pipe fixing member 103 is inclined or is not at the reference position, thus the pipe adjustment unit is operated to correct the inclination of the pipe fixing member 103 (S503). If the conduction is confirmed between the lower resilient members 114, the detected pressure on the piezoelectric elements 402 disposed at the base portions of the lower resilient members is confirmed (S504). If the pressure of the predetermined value or more is detected, it is determined that the pipe fixing member 103 is inclined, thus the pipe adjustment unit is operated to correct the inclination of the pipe fixing member 103. If no pressure of the predetermined value or more is detected, it is determined that the pipe fixing member 103 is at the normal position (FIG. 7A) (S505).

The liquid suction device selects the moving operation of the arm 101 in the X-Y direction or in the Z direction (S506). If the arm 101 is moved in the X-Y axial plane direction (S507), the position and the inclination of the pipe fixing member 103 are confirmed again after the moving operation of the arm 101 is completed (S508).

If the nozzle tip end 201 is moved in the Z axial direction, the arm 101 is moved downward (S509), and the conduction between the resilient members is monitored (S510). If the conduction between the lower resilient members 114 is detected (S511), it is determined that the nozzle tip end 201 is out of contact with the bottom surface of the container 404, and the arm 101 is continued to be moved downward. If the upper resilient members 301 are conducted to each other, and the pipe fixing member 103 is determined to be at the upper limit of the upward movement (S512), or if no conduction is detected between the lower resilient members 114 and between the upper resilient members 301 (S510), the pressure on the piezoelectric elements 402 is confirmed (S513). If no pressure is detected, it is determined that the nozzle tip end 201 is in contact with the bottom surface of the container 404 and then the pipe fixing member 103 is moved upward (S514), so that the downward movement of the arm 101 is stopped. Thereafter, the liquid is sucked from the nozzle tip end 201 (S515), the arm 101 is moved upward (S516), and the movement of the arm 101 is selected (S517) or the liquid suction operation is completed (S518). The liquid discharging operation may be carried out in accordance with the flow of FIG. 9, and the discharge operation may be carried out instead of the suction operation in Step S515.

The descriptions have been provided on the configuration of detecting the position and the inclination state of the pipe fixing member by using the electric conductive resilient members and the pipe fixing member equipped with the conducting layers on the surfaces thereof as well as the configuration of detecting the inclination of the pipe fixing member by disposing the piezoelectric elements at the base portions of the respective resilient members, by describing the embodiment providing the resilient members above and beneath the pipe fixing members, respectively. These configurations, however, may also be applicable to the embodiment with reference to FIG. 1 to FIG. 5 using the resilient members only beneath the pipe fixing members. In addition, the configuration of using the conductive resilient members and the pipe fixing member equipped with the conducting layers on the surfaces thereof and the configuration of disposing the piezoelectric elements at the base portions of the respective resilient members may be employed separately.

It may be configured to always monitor the inclination state of the pipe fixing member, store monitored data on a storage unit and record data regarding the liquid suction operation accomplished normally from start to finish. The monitored data may be used as the certificate that a dispensing operation in a human blood examination has been performed and completed appropriately in the case of incorporating the present invention in an examination apparatus in the medical field, for example. This configuration enables it possible to quickly find out an abnormal step in the dispensing operation if any abnormality is found in the monitored data, so as to prevent important samples from being lost and secure parts replacement.

Hereinafter, descriptions will be provided on the embodiment of detecting microbes by using the liquid suction device and the liquid suction discharge method.

In both the cases with and without the liquid suction device of the present invention, the faint luminous reaction was caused in ATP (Adenosine triphosphate) molecules derived from *Escherichia coli* with firefly luciferase and luciferin in a dark box so as to detect luminescence, and the detected luminescence was converted into ATP amount as the *Escherichia coli* detection sensitivity, and the comparison of the *Escherichia coli* detection sensitivity was made between both the cases.

FIG. 8 is a schematic diagram of an analyzer used in the present embodiment. A sample container having a bottom surface of a membrane filter can be installed in the liquid suction device. The liquid suction device includes the suction unit 802, the waste fluid unit 803, the microbial dissolution solution supply unit 804 for storing the microbial dissolution solution 805, the detection unit 806, the luminescence reagent reservoir 807 for storing the luminescence reagent 808 and these components are housed in the dark box 809. The liquid suction device is operated through the input output unit 810 provided on the outside of the dark box 809. A measurer cannot open the dark box 809 from the installation of the sample container 106 until the completion of the detection of the faint luminous reaction, and cannot visually confirm the position and the inclination state of the nozzle tip end 201 in the dark box 809.

*Escherichia coli* were used as the measurement target microbe. The *Escherichia coli* were suspended in the phosphate buffer of pH 7.4 (manufactured by Invitrogen Corporation) so as to prepare the *Escherichia coli* suspension whose cell density is 300 cells/300 µL.

Figure 10:
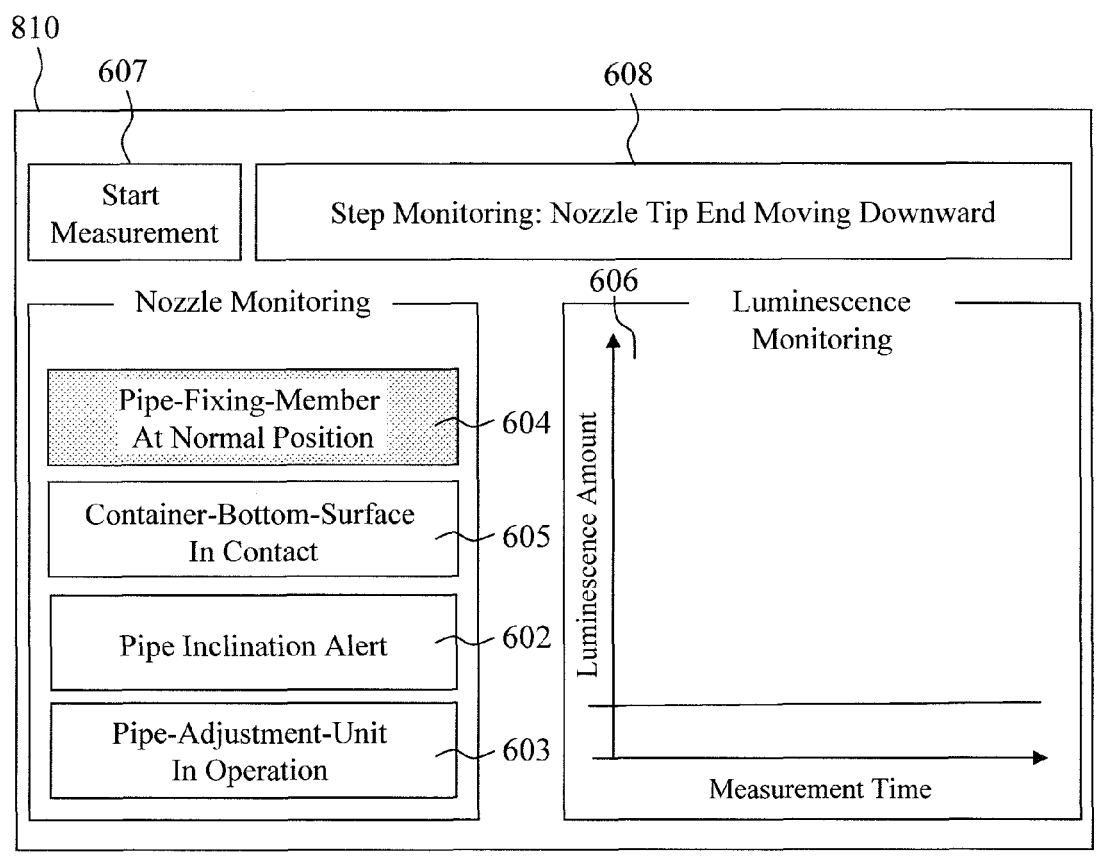
FIG. 10 is a drawing of illustrating a display screen of an input output unit.

The *Escherichia coli* suspension of 10 mL was added into the respective membrane filters in the sample container 106, and the ATP erasing solution of 10 µL as a biological-material-excluding-microbe removal reagent, which was attached to the Lucifell HS Set (manufactured by Kikkoman Corporation), was further added, and the sample container 106 was housed in the dark box 809, and then the dark box 809 was closed. FIG. 10 is a drawing of illustrating the display screen of the input output unit 810. This input output unit displays the position of the nozzle tip end and the inclination state of the pipe fixing member in accordance with the operation procedure as illustrated in FIG. 9. The step monitoring display 608 displays the current step of the nozzle operation.

The *Escherichia coli* suspension and the ATP erasing solution were filtered through the membrane filter 110 by using the suction unit 802. After the filtering, the nozzle tip end 201 sucked the ATP extract of 300 µL, which was attached to the Lucifell HS Set as the microbial dissolution solution 805, from the microbial dissolution solution supply unit 804, and discharged this ATP extract onto the membrane filter 110, so as to extract the ATP molecules from the *Escherichia coli*. The nozzle tip end 201 was moved downward to come in contact with the membrane filter 110, so as to suck the microbial dissolution solution remained on the membrane filter 110 into the pipe 102, and discharged the sucked microbial dissolution solution into the luminescence reagent 808 (luminescence reagent of 200 µL, attached to the Lucifell HS Set) in the luminescence reagent reservoir 807 disposed on the detection unit 806 with the nozzle tip end 201 in contact with the bottom surface of the luminescence reagent reservoir 807. Since the bottom surface of the luminescence reagent reservoir 807 was nearest to the detection unit 806, and discharging the sucked microbial dissolution solution 805 at this position enables the most efficient detection of the generated luminescence by the detection unit 806. In the case of discharging the sucked microbial dissolution solution with the nozzle tip end 201 out of contact with the bottom surface, the detection sensitivity was decreased.

As described above, in the case of using the liquid suction device of the present invention, it is possible to monitor the position and the inclination state of the pipe fixing member 103 on the input output unit 810 at any time. The input output unit 810 is a touch panel display. For example, if the pipe fixing member 103 becomes inclined, the inclination of the pipe fixing member 103 is detected in the inclination determination steps, S502, S504, S513, and the detected result is confirmed by the display on the pipe inclination alert display 602 in the input output unit 810. If it is determined that the pipe fixing member 103 is inclined, the background color of the pipe inclination alert display 602 is changed, for example. In this case, it is possible to confirm that the inclination correction is being performed by adjusting the pipe length on the pipe adjustment unit 801 in the pipe-adjustment-unit operation step S503 through the pipe-adjustment-unit in operation display 603 of the input output unit 810, and after the correction, it is also possible to confirm that the pipe fixing member is located at the normal position in the normal position determination step S506 through the pipe-fixing-member at normal position display 604 of the input output unit 810.

It is possible to confirm that the nozzle tip end 201 comes in contact with the membrane filter 110 without the inclination of the pipe fixing member 103 in the container-bottom-surface contact determination step S514 through the container-bottom-surface in contact display 605 of the input output unit 810, and the luminescence resulted from the faint luminance reaction can be observed through the luminescence monitoring display 606. The input output unit 810 further includes the measurement start button 607 and the step monitoring display 608 for informing the current step. Meanwhile, in the case without the liquid suction device of the present invention, only luminous reaction spectra were acquired.

Based on the result from ten trials, the result in the case of employing the present invention was 1.36 amol ATP per *Escherichia coli* cell on average, along with SD 0.01 amol ATP, and C.V. 1%. To the contrary, the result in the case without employing the present invention was 0.95 amol ATP per *Escherichia coli* cell on average, along with SD 0.34 amol ATP, C.V. 35.4%; therefore, in the case of the present invention, the average value, SD and C.V. were all improved.

Figure 11A:
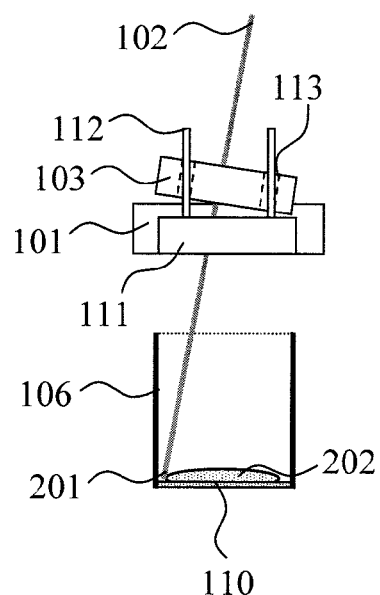
FIG. 11A is a drawing of explaining a problem caused in the case without employing the present invention.
Figure 11B:
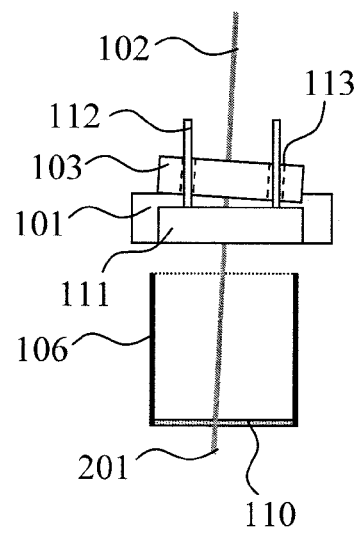
FIG. 11B is a drawing of explaining a problem caused in the case without employing the present invention.
Figure 11C:
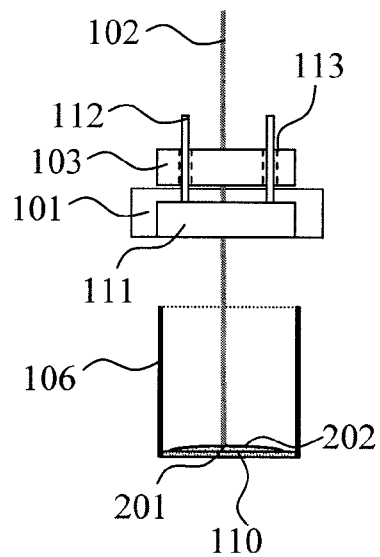
FIG. 11C is a drawing of explaining a problem caused in the case without employing the present invention.

In the case without employing the present invention, no luminescence was detected in some cases. Every time no luminescence was detected, the dark box was opened for inspection of the inside of the device, and as illustrated in FIG. 11A, it was found that the length of the pipe 102 was too short when the arm 101 moved downward, so that the pipe fixing member 103 became inclined and the rails 112 on the rail base 111 were caught by the through holes 113, thus the nozzle tip end 201 also became inclined and could not suck the droplet 202 on the membrane filter 110. It was also found that, as illustrated in FIG. 11B, the pipe fixing member 103 became inclined and could not move vertically, and the nozzle tip end 201 pierced the membrane filter 110 so that the sample droplet was lost; or as illustrated in FIG. 11C, the pipe fixing member 103 was not at the reference position, so that the nozzle tip end 201 could not come in contact with the droplet 202 on the membrane filter so that no droplet was sucked, which resulted in no detection of luminescence.

In the case of employing the present invention, it was possible to efficiently suck the droplet on the membrane filter, and improved the microbe detection sensitivity.

REFERENCE SIGNS LIST

101 Arm
102 Pipe
103 Pipe fixing member
104 Pump
105 Controller
106 to 108 Sample containers
109 Sample container stand
110 Membrane filter
111 Rail base
112 Rails
113 Through hole
114 Resilient member
121 Upper rail base
201 Nozzle tip end
202 Droplet
301 Resilient member
401 Conducting layer
402 Piezoelectric element
403 Piezoelectric element
404 Container bottom surface
602 Pipe inclination alert display
603 Pipe-adjustment-unit in operation display
604 Pipe-fixing-member at normal position display
605 Container-bottom-surface in contact display
606 luminescence monitoring display
607 Measurement start button
608 Step monitoring display

The invention claimed is:

1. A liquid suction device comprising:
an arm movable in three-dimensional directions;
plural rails disposed parallel to each other so as to extend upward from the arm;
a pump;
a pipe having a body, a tip end for functioning as a nozzle, and having a rear end connected to the pump;
a pipe fixing member to which pipe is fixed, having plural through holes for inserting the plural rails therethrough, and movable relative to the arm along the plural rails; and
plural resilient members fixed to the arm so as to be disposed between the arm and the pipe fixing member;
wherein:
the resilient members are conductive,
the pipe fixing member has a conducting layer on a surface thereof to permit electrical conduction between ones of the resilient members, when ones of the resilient members are in contact with the pipe fixing member, and
the liquid suction device further comprises a controller electrically connected to the resilient members to detect electrical conduction states between the ones of the resilient members, the controller configured to determine a position and an inclination of the pipe fixing member relative to the plural rails, based on the electrical conduction states detected between the ones of the resilient members.

2. The liquid suction device according to claim 1, wherein the liquid suction device further comprises an upper rail base fixed onto upper ends of the plural rails, and upper plural resilient members are fixed to the upper rail base so as to be disposed between the upper rail base and the pipe fixing member.

3. The liquid suction device according to claim 1, wherein
the resilient members are springs, rubber, sponge or magnets, and
when the resilient members are magnets, a portion of the pipe fixing member opposing the resilient members includes magnets with a same pole as that of the magnets of the resilient members.

4. The liquid suction device according to claim 1, wherein the plural rails are three or more, and the resilient members are disposed on or outside a polygon defined by connecting the plural rails.

5. The liquid suction device according to claim 1, wherein the plural rails extend above the pipe fixing member, and
wherein the pipe fixing member is capable of moving upwards along the plural rails when the tip end of the pipe is brought into contact with a bottom surface of a container so as to suck liquid in the container.

6. The liquid suction device according to claim 1, further comprising:
piezoelectric elements disposed at base portions of the respective resilient members, and
wherein the controller is configured to determine an inclination state of the pipe fixing member based on pressures detected by the piezoelectric elements.

7. The liquid suction device according to claim wherein
the liquid suction device further comprises a pipe adjustment unit including a rotor around which the pipe is wound and disposed between the pipe fixing member and the pump, and
wherein the pipe adjustment unit is configured to adjust a length of the pipe between the pipe adjustment unit and the pipe fixing member by rotating the rotor when an inclination at a predetermined amount of the pipe fixing member is detected.

8. The liquid suction device according to claim 1, further comprising:
a pipe adjustment unit disposed between the pipe fixing member and the pump, and having a rotor around which the pipe is wound so as to adjust a length of the pipe between the pipe fixing member and the pipe adjustment unit by rotating the rotor,
wherein the controller is configured to confirm conduction between the resilient members through the conducting layer of the pipe fixing member before the arm is moved,
wherein the controller is configured to determine that the pipe fixing member is located at a normal position by detecting conduction between the resilient members through the conducting layer of the pipe fixing member,
wherein the controller is configured to determine that the pipe fixing member is located at an abnormal position by detecting no conduction between the resilient members through the conducting layer of the pipe member,
wherein the controller is configured to correct the pipe fixing member into the normal position by adjusting the length of the pipe by using the pipe adjustment unit when determined that the pipe fixing member is located at the abnormal position,
wherein the controller is configured to move the arm in a target direction and monitor the conduction between the resilient members all the time during the movement of the arm when determined that the pipe fixing member is located at the normal position,
wherein the controller is configured to stop downward movement of the arm when no conduction between the resilient members is detected while the arm is being moved in a height direction, and
wherein controller is configured to suck liquid in a container from the tip end of the pipe.

9. The liquid suction device according to claim 2, further comprising:
a pipe adjustment unit between the pipe fixing member and the pump, and having a rotor around which the pipe is wound so as to adjust a length of the pipe between the pipe fixing member and the pipe adjustment unit by rotating the rotor,
wherein the controller is configured to determine that the pipe fixing member is located at a normal position when the resilient members fixed to the arm are conducted to each other through the conducting layer, and
wherein the controller is configured to determine that the pipe fixing member is at an upper limit of a vertical movement along the plural rails when the upper resilient members fixed to the upper rail base are conducted to each other through the conducting layer.

10. The liquid suction device according to claim 9, wherein the controller is configured to:
determine that the pipe fixing member is inclined when conduction is made between the resilient members fixed to the arm and the upper resilient members fixed to the upper rail base, and
adjust the length of the pipe by using the pipe adjustment unit so as to correct the inclination of the pipe fixing member.

11. The liquid suction device according to claim 8, further comprising:
a recording unit;
wherein:
the controller is configured to:
monitor an inclination state of the pipe fixing member all of the time,
store the monitored data in the recording unit, and
record data regarding a liquid suction operation normally accomplished from start to finish, in the recording unit.

12. The liquid suction device according to claim 8, further comprising:
a reagent reservoir for storing a microbial dissolution solution;
a sample container equipped with a membrane filter at a bottom portion thereof;
a suction unit for sucking liquid in the sample container through the membrane filter;
a reagent container for storing luminescence reagent; and
a detection unit for detecting luminescence, and
wherein the controller is configured to:
supply a sample containing microbes in the sample container,
filter the sample through the membrane filter by using the suction unit so as to capture the microbes on the membrane filter,
suck the microbial dissolution solution in the reagent reservoir from the tip end of the pipe,
discharge the sucked microbial dissolution solution onto the membrane filter,
bring the tip end of the pipe into contact with the membrane filter so as to suck the microbial dissolution solution again,
discharge the sucked microbial dissolution solution into luminescence reagent in the luminescence reagent container, and
detect generated luminescence on the detection unit.

13. The liquid suction device according to claim 6, further comprising:

a pipe adjustment unit including a rotor around which the pipe is wound and disposed between the pipe fixing member and the pump, and wherein the pipe adjustment is configured to adjust a length of the pipe between the pipe adjustment unit and the pipe fixing member by rotating the rotor when an inclination at a predetermined amount of the pipe fixing member is detected.

14. The liquid suction device according to claim 9, further comprising:

a recording unit;

wherein the controller is configured to:

monitor an inclination state of the pipe fixing member all of the time, store the monitored data in the recording unit, and record data regarding a liquid suction operation normally accomplished from start to finish, in the recording unit.

15. The liquid suction device according to claim 9, further comprising:

a reagent reservoir for storing a microbial dissolution solution;

a sample container equipped with a membrane filter at a bottom portion thereof;

a suction unit for sucking liquid in the sample container through the membrane filter;

a reagent container for storing luminescence reagent; and a detection unit for detecting luminescence, and wherein the controller is configured to:

supply a sample containing microbes in the sample container, filter the sample through the membrane filter by using the suction unit so as to capture the microbes on the membrane filter, suck the microbial dissolution solution in the reagent reservoir from the tip end of the pipe, discharge the sucked microbial dissolution solution onto the membrane filter, bring the tip end of the pipe into contact with the membrane filter so as to suck the microbial dissolution solution again, discharge the sucked microbial dissolution solution into luminescence reagent in the luminescence reagent container, and detect generated luminescence via the detection unit.

16. The liquid suction device according to claim 1, wherein the arm is movable in a vertical direction, wherein the plural rails are fixed to the arm, wherein the tip end of the pipe is fixed downward with respect to the pipe fixing member, wherein the pipe fixing member is disposed above the arm and is vertically movable relative to the arm along the plural rails, and wherein the plural resilient members are not fixed to the pipe fixing member so as to independently act on the pipe fixing member.

17. The liquid suction device according to claim 1, wherein the pipe fixing member is in contact with the plural resilient members by its own weight.

* * * * *